United States Patent [19]

Okazaki

[11] Patent Number: 4,773,396
[45] Date of Patent: Sep. 27, 1988

[54] ENDOSCOPE

[75] Inventor: Tsugio Okazaki, Hachioji, Japan

[73] Assignee: Olympus Optical Co., Ltd., Tokyo, Japan

[21] Appl. No.: 77,917

[22] Filed: Jul. 27, 1987

[30] Foreign Application Priority Data

Aug. 11, 1986 [JP] Japan .................. 61-189242

[51] Int. Cl.⁴ .............................................. A61B 1/00
[52] U.S. Cl. ......................................... 128/6; 358/98
[58] Field of Search .......................... 128/4, 6; 358/98

[56] References Cited

U.S. PATENT DOCUMENTS

| 4,573,450 | 3/1986 | Arakawa | 128/6 |
| 4,622,954 | 11/1986 | Arakawa et al. | |
| 4,663,657 | 5/1987 | Nagasaki et al. | 128/6 X |
| 4,667,656 | 5/1987 | Yabe | 128/6 |
| 4,692,608 | 9/1987 | Cooper et al. | 128/6 X |

Primary Examiner—William H. Grieb
Attorney, Agent, or Firm—Armstrong, Nikaido, Marmelstein & Kubovcik

[57] ABSTRACT

This electronic endoscope is provided with a flexible insertable part formed to be small in the diameter. A plurality of components provided in parallel are included within the insertable part tip. A second largest component which has a contour smaller than the contour of a solid state imaging device which is one of the above mentioned components but larger than those of the other components and in which at least a part of the contour overlaps on an imaginary circle having the smallest diameter including the contour of the above mentioned solid state imaging device with the center of the solid state imaging device as a center is included. An objective system having an optical axis coinciding with the center of the above mentioned image area is included.

17 Claims, 5 Drawing Sheets

ENDOSCOPE

FIELD OF THE INVENTION

This invention relates to an electronic endoscope wherein the diameter of the insertable part can be made smaller.

BACKGROUND OF THE INVENTION AND RELATED ART STATEMENT

Various endoscopes (which shall be called electronic endoscopes in the present invention) wherein such solid state imaging devices as charged coupled devices (CCD's) are used for imaging means have been recently suggested.

Such electronic endoscope has advantages that the resolving degree is higher than in a fiberscope, the recording and reproduction of picture images are easy and such picture image processes as the magnification of picture images and comparison of two picture surfaces are easy.

With the above mentioned endoscope, a body cavity interior or the like can be observed by inserting the insertable part of a fine diameter into the body cavity or a curing treatment can be made with a treating tool. Therefore, in order to reduce a pain to the patient when the insertable part is inserted, it is desirable to make the tip of the above mentioned insertable part fine. In order to meet such desire, in the specification of U.S. Pat. No. 4,622,954, there is disclosed a technique wherein a solid state imaging device is arranged in parellel with the lengthwise direction of an insertable part so that such other components as, for example, a forceps channel, light guide and air and water feeding tube may be effectively arranged and the outside diameter of the insertable part may be made small.

It is also desirable that the tip of the insertable part is in such form easy to insert into a body cavity as, for example, a tapered form but the form of this tip is restricted by the sizes and arrangements of components provided within this tip.

In the above mentioned electronic endoscope, such components as not only an imaging means having an objective system as an image forming optical system and a solid state imaging device but also a forceps channel, air and water feeding tube and light guide are generally internally provided in the above mentioned tip. In comparing the sizes in the cross-section of the above mentioned respective components including the above mentioned solid state imaging device, it is found that generally the above mentioned solid state imaging device is the largest, to be followed by the forceps channel and light guide in the order mentioned. By the way, in case the observing performance is particularly considered to be more important than the processing perfromance, the sizes will be in the order of the solid state imaging device, light guide and forceps channel.

Now, it is considered that the tip will be able to be made the finest if the above mentioned solid state imaging device and the second largest component (generally the forceps channel) next to this solid state imaging device are arranged adjacently to each other. Also, in case the above mentioned solid state imaging device is, for example, square, the tip will be able to be made fine to some extent by arranging the above mentioned second largest component on the side of this solid state imaging device.

Further, in order to make small the outside diameter of the tip on the tip side beyond the above mentioned solid imaging device, the objective system and the second largest component, for example, the forceps channel may be set to be close to each other.

Now, conventionally, in the above mentioned solid state imaging device, a chip on which many light receiving elements (picture elements) are arranged is arranged in the central part and is electrically connected with leads provided in a package through bonding wires or the like. Therefore, the entire solid state imaging device is larger than the size of the image area of the above mentioned chip. Also, generally, the outside diameter of the above mentioned solid state imaging device is larger than that of the objective system.

As mentioned above, conventionally, the position of the above mentioned objective system has been restricted by the size of the above mentioned solid state imaging device and it has not been considered to arrange the above mentioned objective system and the second largest component to be close to each other so that the outside diameter of the tip on the tip side beyond the solid state imaging device may be made smaller and the tip may be in the form easy to insert into a body cavity.

OBJECTS AND SUMMARY OF THE INVENTION

An object of the present invention is to provide an electronic endoscope wherein the tip of the insertable part can be made finer or formed to be easy to insert into a body cavity.

In the present invention, the tip of an insertable part has an imaging means consisting of a solid state imaging device and an image forming optical system forming the image of an object in the image area of this solid state imaging device and a second largest component smaller than the above mentioned solid state imaging device but larger than the other components in the cross-section and the above mentioned solid state imaging device and second largest component are arranged to be adjacent to each other so that at least a part of the above mentioned second largest component may overlap on the smallest circle including the solid state imaging device in a cross-section including this solid state imaging device.

Other features and advantages of the present invention will become apparent enough with the following explanation.

BRIEF DESCRIPTION OF THE DRAWINGS

FIG. 1 is a side view showing an entire electronic endoscope.

FIG. 2 is a cross-sectioned view of a tip of the insertable part of the electronic endoscope.

FIG. 3 is a longitudinally sectioned view of the tip.

FIG. 4 is a block diagram showing a video signal processing circuit.

FIG. 5 is a sectioned view of a tip of the insertable part of the electronic endoscope.

FIG. 6 is a front view of the tip.

FIG. 9 is a sectioned view of a solid state imaging device part of the tip of the insertable part of an electronic endoscope.

FIG. 10 is a sectioned view of a substrate of the tip.

DETAILED DESCRIPTION OF PREFERRED EMBODIMENTS:

The embodiments of the present invention shall be explained in the following with reference to the drawings.

Figure 1:
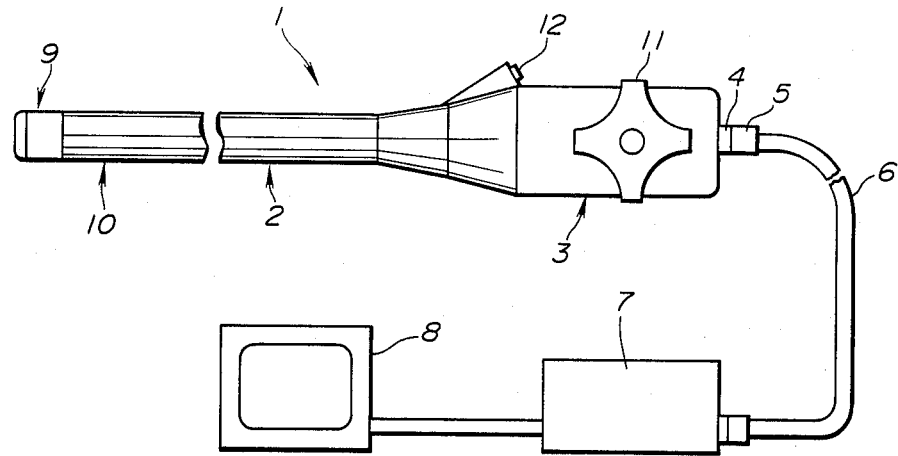
FIGS. 1 to 4 relate to the first embodiment of the present invention.

As shown in FIG. 1, in an electronic endoscope 1, a thick operating part 3 is connected to the rear end of an elongated and, for example, flexible insertable part 2. A connector receiver 4 is provided at the rear end of the above mentioned operating part 3. The above mentioned operating part 3 and a controlling part 7 containing a light source device and a video signal processing circuit are to be connected with each other through a cable 6 having a connector 5 to be fitted to this connector receiver 4. Further, a color CRT monitor 8 as a displaying means is to be connected to the above mentioned controlling device 7.

A rigid tip 9 and a curvable part 10 curvable rearward and adjacent to this tip 9 are provided in turn on the tip side of the above mentioned insertable part 2. Also, by rotating and operating a curving operation knob 11 provided on the above mentioned operating part 3, the above mentioned curvable part 10 can be curved horizontally and vertically. An inserting port 12 communicating with a forceps channel provided within the above mentioned insertable part 2 is provided in the above mentioned operating part 3.

Figure 2:
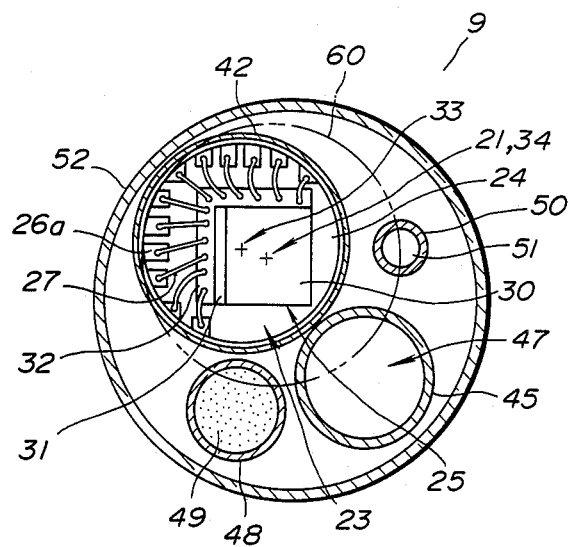
Figure 3:
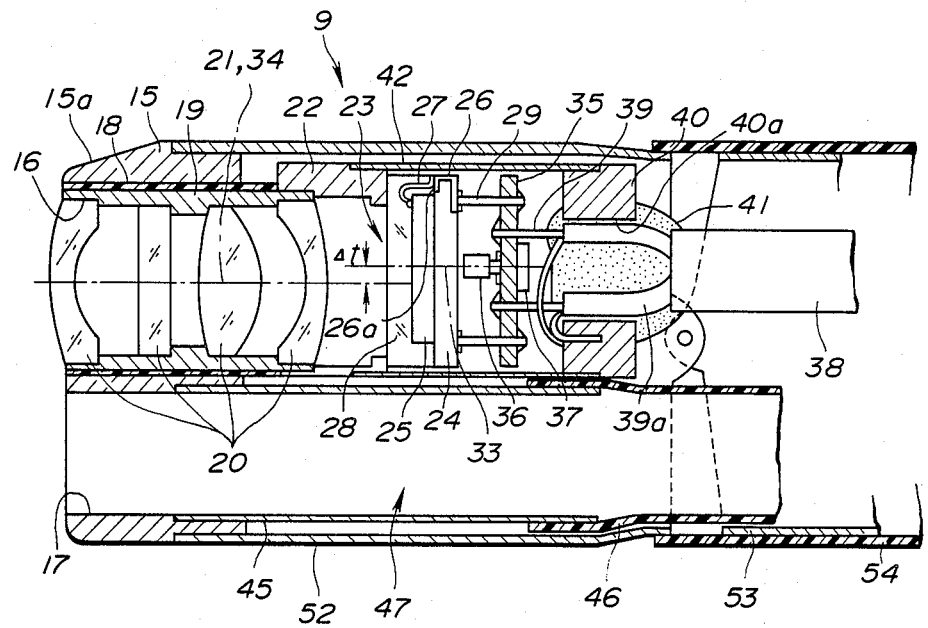

The above mentioned tip 9 is formed as shown in FIGS. 2 and 3.

That is to say, the tip 9 is provided with a substantially columnar tip body 15 made of such rigid material as a metal. An observing through hole 16 passing parallelly with the lengthwise direction of the above mentioned insertable part 2 and a forceps channel through hole 17 and an illuminating through hole and an air and water feeding through hole not illustrated are formed in this tip body 15.

A lens frame 19 is fitted to the above mentioned observing through hole 16 through an insulating frame 18. An objective system 20 as an image forming optical system is held by the above mentioned lens frame 19 so that its optical axis 21 may be parallel with the lengthwise direction of the above mentioned insertable part 2.

A devide holder 22 is connected to the rear end of the above mentioned lens frame 19. A solid state imaging device 23 is fixed to the rear end of this device holder 22.

In this solid state imaging device 23, for example, a disc-like base 24, a solid state imaging chip 25 fixed on this base 24, a plurality of leads 26 provided on the above mentioned base 24, bonding wires 27 electrically connecting the plurality of leads 26 with the above mentioned solid state imaging chip 25, a protective layer 28 made of a transparent resin or the like covering the above mentioned bonding wires 27 and feet 29 provided on the opposite imaging chip side of the above mentioned base 24 and electrically connected respectively with the above mentioned leads 26 are formed in an integral package. The above mentioned protective layer 28 is secured to the rear end of the above mentioned device holder 22.

As shown in FIG. 2, the above mentioned solid state imaging chip 25 has a rectangular image area 30 on which an object image is formed by the above mentioned objective system 20, an optical black row 31 for detecting a black level and a bonding pad 32 for connecting the above mentioned bonding wires 27 with this solid state imaging chip 25.

In this embodiment, a part in which the optical black row 31 and such bonding parts as the bonding pad 32, bonding wires 27 and leads 26 are not located is provided between the image area 30 of the above mentioned solid state imaging device 23 and the outer periphery of the package and the above mentioned image area 30 is arranged to be close to the outer peripheral side from the center of the package of the solid state imaging device. That is to say, the above mentioned bonding pad 32 is arranged to be L-shaped along the two sides of the above mentioned image area 30 reverse to the outer peripheral side of the package. The above mentioned optical black row 31 is adjacent to the side of the above mentioned image area 30 reverse to the outer peripheral side of the package. Electrode pads 26a of the above mentioned leads 26 connected to the above mentioned bonding pad 32 through the bonding wires 27 are arranged along the outer periphery of the package (base 24) so as to enclose the solid state imaging chip 25 as opposed to the above mentioned bonding pad 32. This is because there is a minimum limit to the spacing of the electrode pads 26a and, if the electrode pads 26a are arranged in the same arranged form as of the bonding pad 32 of the solid state imaging chip 25, the base 24 will become large. By arranging the electrode pads 26a so as to enclose the solid state imaging chip 25, the base 24 can be made small, that is, the solid state imaging device 23 can be made small to make the tip small in the diameter.

Also, the above mentioned solid state imaging device 23 is so arranged that the center 34 of the above mentioned image area 30 may coincide with the optical axis 21 of the above mentioned objective system 20.

The feet 29 of the above mentioned solid state imaging device 23 are connected to a substrate 35. Such electric parts forming the driving circuit of the above mentioned solid state imaging device 23 and preamplifiers as, for example, a transistor 36 and condenser 37 are fitted, for example, to both surfaces of this substrate 35. Leads 39 of a cable 38 conducting to the above mentioned solid state imaging device 23, transistor 36 and condenser 37 through a wiring pattern not illustrated are connected to this substrate 35. The coated parts 39a of these leads 39 are inserted through a cable inserting hole 40a of a cable fixing member 40 provided on the substrate side of the above mentioned substrate 35. This cable inserting hole 40a is filled, for example, with a cement 41 to fix the coated parts 39a of the above mentioned leads 39. Even if the above mentioned cable 38 is pulled, no force will be applied to the connecting parts of the leads 39 with the substrate 35 to prevent the leads from being broken. The above mentioned cable 38 is inserted through the above mentioned insertable part 2 and is connected to the connector receiver 4 of the above mentioned operating part 3.

The above mentioned solid state imaging device 23 and substrate 35 between the above mentioned device holder 22 and cable fixing member 40 are covered, for example, with a cylindrical shield pipe 42.

On the other hand, a forceps mouthpiece 45 is fitted in the above mentioned forceps channel through hole 17. A forceps channel tube 46 forming a forceps channel 47 as a second largest component smaller than the above mentioned solid state imaging device 23 in the size in the cross-section but larger than the other components as shown in FIG. 2 is connected to the rear end of this forceps mouthpiece 45. This forceps channel tube 46 is inserted through the above mentioned insertable part 2 and is connected to the above mentioned inserting port 12.

A light distributing lens system (not illustrated) is fitted in an illuminating through hole (not illustrated). A light guide 49 coated with a light guide tube 48 is connected to the rear end of this light distributing lens system. This light guide 49 is inserted through the above mentioned insertable part 2 and is connected to the connector receiver 4 of the above mentioned operating part 3.

The cable 6 to be connected to the above mentioned connector receiver 4 through the connector 5 is provided with a cable transmitting a signal from the above mentioned cable 38 to the controlling device 7 and a light guide transmitting a light from the light source device within the controlling device 7 to the above mentioned light guide 49.

An air and water feeding nozzle (not illustrated) is fitted to an air and water feeding channel through hole not illustrated. An air and water feeding tube 50 forming an air and water feeding channel 51 is connected to this air and water feeding nozzle. This air and water feeding tube 50 is inserted through the above mentioned insertable part 2 and is connected to an air and water feeding port not illustrated provided in the above mentioned operating part 3.

The solid state imaging device 23 which is a component of the above mentioned tip 6, the forceps mouthpiece 45 forming the forceps channel 47, the light guide 49 coated with the light guide tube 48 and the air and water feeding tube 50 forming the air and water feeding channel 51 are covered with a tip outer tube 52 connected to the rear end side of the above mentioned tip body 15. Many articularing frames 53 are connected in the lengthwise direction of the insertable part 2 to form the curvable part 10. Also, the above mentioned articulating frames 53 are covered with a soft tube 54 forming a jacket tube for the above mentioned insertable part 2.

In this embodiment, as shown in FIG. 2, the above mentioned solid state imaging device 23 and forceps channel 47 are arranged adjacently to each other so that a part of the forceps channel 47 as the second largest component may largely overlap on the smallest circle 60 including this solid state imaging device 23 in the cross-section including this solid state imaging device 23 with the center 34 of the image area 30 of the above mentioned solid state imaging device 23 as a center. That is to say, the forceps channel 47 is arranged on the side on which the optical black row 31 and such bonding part as the bonding pad 32 are not located between the image area 30 of the solid state imaging device 23 and the outer periphery of the package.

By thus arranging the solid state imaging device 23 and forceps channel 47, the above mentioned image area 30 and forceps channel 47 can be brought to be close to each other. As a result, the objective system 20 in which the optical axis 21 coincides with the center 34 of the above mentioned image area 30 is brought to be close to the above mentioned forceps channel 47. In this embodiment, for example, as compared with the case that the image area 30 is arranged in the center of the package of the solid state imaging device 23, in FIG. 3, the objective system 20 and forceps channel 47 are brought to be close to each other by $\Delta t$.

The tip side beyond the solid state imaging device 30 of the tip 9 can be made smaller in the diameter by the part by which the above mentioned objective system 20 and forceps channel 47 are brought to be closer to each other. In this embodiment, as shown in FIG. 3, the side part 15a on the side reverse to the above mentioned forceps channel 47 of the above mentioned tip body 15 is formed to be tapered to be smaller in the diameter on the tip side so as to be easy to insert into a body cavity.

Now, the light source device provided within the above mentioned controlling device 7 is provided, for example, with a light source lamp and a rotary color filter consisting of color transmitting filters of the three primary colors of red, green and blue in the case of a field sequential system so that the illuminating light of the above mentioned light source lamp may be made lights of the respective wavelengths of red, green and blue in sequence through the above mentioned rotary color filter. This illuminating light is projected out of the tip of a light distributing lens system not illustrated through the above mentioned cable 6, light guide 49 and light distributing lens system to illuminate an object in the color field sequence.

Figure 4:
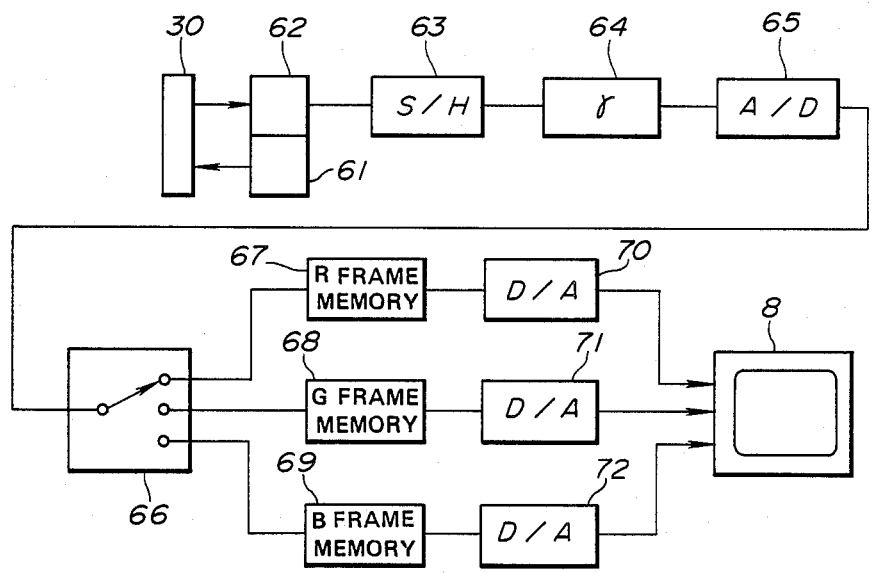

The reflected lights corresponding to the respective colors of red, green and blue from the above mentioned object are received in sequence by the image area 30 of the above mentioned solid state imaging device 23 through the objective system 20. The output signal of this solid state imaging device 23 is processed to be an image signal, for example, as shown in FIG. 4 in the case of a field sequential system. That is to say, the signals corresponding to the respective picture elements of the above mentioned solid state imaging device 30 are output in sequence, for example, in the lateral direction by clock signals applied from a driving circuit 61. These picture element signals are amplified by a preamplifier 62, are extracted as image signals by a sample holding circuit 63, are further $\gamma$-corrected by a $\gamma$-correcting circuit 64 and are then converted to digital signals by an A/D converter 65. These image signals are switched as synchronized with a color field sequential illumination by a multiplexer 66 and are memorized in sequence in an R (red) frame memory 67, G (green) frame memory and B (blue) frame memory 69 corresponding to the respective colors of red, green and blue. The above mentioned respective frame memories 67, 68 and 69 are simultaneously read out in the lateral direction at a speed matching such displaying device as a color CRT monitor 8 and are converted to analogue signals respectively by D/A converters 70, 71 and 72 to be R, G and B color signals. These R, G and B signals are output to the color monitor 8 to color display the object.

Thus, in this embodiment, the image area 30 of the solid state imaging device 23 is arranged to be close to the outer peripheral side of the package and the above mentioned solid state imaging device 23 and forceps channel 47 are arranged to be adjacent to each other so that a part of the forceps channel 47 as the second largest component may largely overlap on the smallest circle 60 including this solid state imaging device 23 in the cross-section including this solid state imaging device 23 with the center 34 of this image area 30 as a center.

By such arrangement, the above mentioned image area 30 and forceps channel 47 are brought to be close to each other and the objective system 20 in which the optical axis coincides with the center 34 of the image area 30 is brought to be close to the above mentioned forceps channel 47. As a result, the tip side beyond the solid state imaging device 23 of the tip 9 can be made small in the diameter and this tip side 9 can be formed to be easy to insert into the body cavity, for example, can be tapered as in this embodiment.

By the way, in case the second largest component smaller in the cross-section than the solid state imaging device 23 but larger than the other components is not limited to be forceps channel 47 but is, for example the light guide 49, the above mentioned image area 30 and light guide 49 may be arranged to be close to each other.

It is needless to say that the imaging system is not limited to be a field sequential system by which the illuminating light is switched in sequence to red, green and blue but may be a simultaneous system in which a color mosaic filter is arranged in front of the imaging surface of the solid state imaging device 23.

Figure 5:
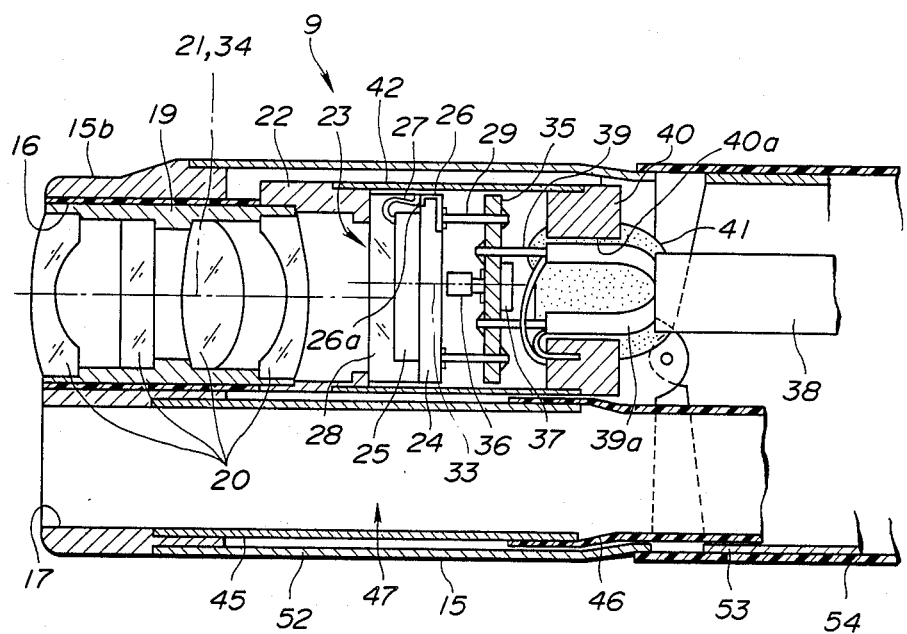
FIGS. 5 and 6 relate to the second embodiment of the present invention.
Figure 6:
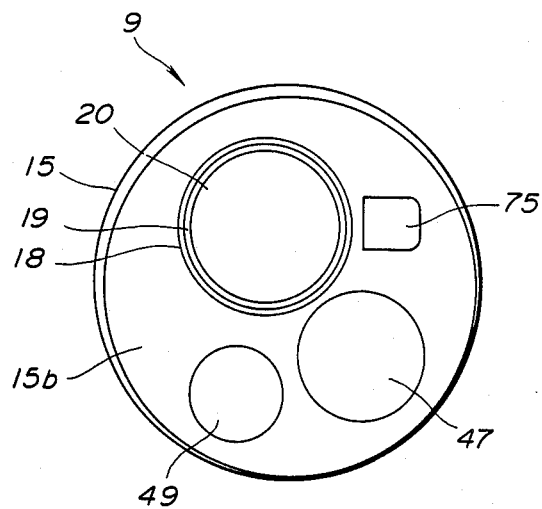

FIGS. 5 and 6 relate to the second embodiment of the present invention. FIG. 5 is a sectioned view of a tip of the insertable part of an electronic endoscope. FIG. 6 is an elevation of the tip.

In this embodiment, the same as in the first embodiment, the image area 30 of the solid state imaging device 23 and the forceps channel 47 are arranged to be close to each other and the outside diameter of the foremost tip part 15b on the tip side of the tip body 15 is made smaller than the outside diameter of the part including the solid state imaging device 23 of the tip body 15.

By the way, in the drawing, the reference numeral 75 represents an air and water feeding nozzle.

Other functions and effects are the same as in the first embodiment.

Figure 7:
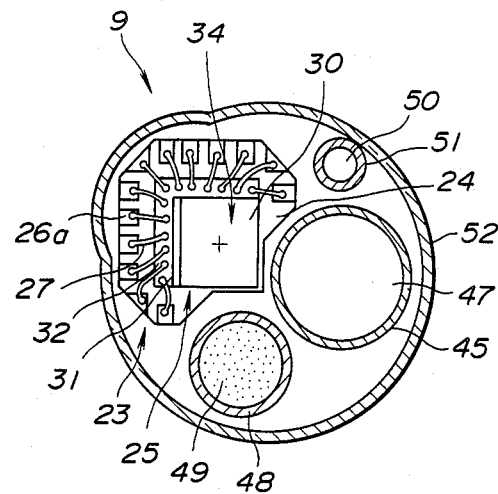
FIG. 7 is a sectioned view of a tip of the insertable part of an electronic endoscope of the third embodiment of the present invention.

FIG. 7 is a sectioned view of a tip of the insertable part of an electronic endoscope of the third embodiment of the present invention.

In this embodiment, the image area 30 of the solid state imaging device 23, optical black row 31 and bonding parts are arranged the same as in the first embodiment but the base 24 is not formed to be disc-like but is formed along the outer periphery of the image area 30 and bonding parts. By thus forming the base 24, as shown in the drawing, the forceps channel 47 as the second largest component can be arranged on the side of the above mentioned image area 30 so that this image area and the forceps channel 47 may be closer to each other.

Also, in this embodiment, the outer tube 52 of the tip is not cylindrical but is protruded ouly on the bonding part side of the above mentioned solid state imaging device to prevent the entire tip 9 from becoming thick.

Figure 8:
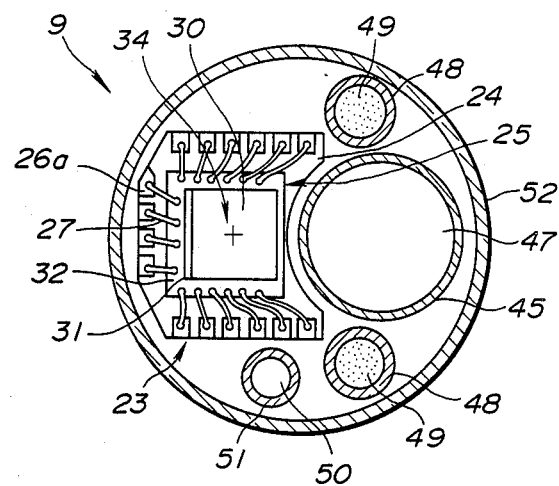
FIG. 8 is a sectioned view of a tip of the insertable part of an electronic endoscope of the fourth embodiment of the present invention.

FIG. 8 is a sectioned view of a tip of the insertable part of an electronic endoscope of the fourth embodiment of the present invention.

In this embodiment, such bonding parts as the bonding pad 32 are arranged on the three sides of the image area 30 of the solid state imaging device 23 and the forceps channel 47 as the second largest component is arranged on the side on which the bonding parts are not formed. The optical black row 31 is arranged on the side reverse to the above mentioned forceps channel 47. The forceps channel 47 side of the base 24 is formed along the outer periphery of this forceps channel 47 so that the above mentioned image area 30 and forceps channel 47 may be close to each other.

Also, in this embodiment, the light guide 49 is divided into two so that the space within the tip 9 may be utilized effectively to make the tip 9 small in the diameter.

On what side of the image area 30 such bonding parts as the bonding pad 32 are to be provided depends on the size of the image area and the number of the leads 26 but, anyhow, by arranging the forceps channel 47 on the side on which the bonding parts are not formed as in this embodiment, the image area 30 and forceps channel 47 can be made close to each other to make the tip 9 small in the diameter.

In the case that, for example, the image area 30 is so small and the leads 26 are so many that it is necessary to form the bonding parts on the entire periphery of the image area 30, by arranging the forceps channel 47 in the direction in which there is no optical black row 31, the image area 30 and forceps channel 47 can be made closer to each other to make the tip 9 smaller in the diameter than in the case that the forceps channel 47 is arranged in the direction in which the optical black row 31 is located.

By the way, it is needless to say that, in the case that the package of the solid state imaging device 23 is, for example, rectangular in the crosssection, by arranging the forceps channel 47 on the long side, the tip 9 can be made small in the diameter.

Figure 9:
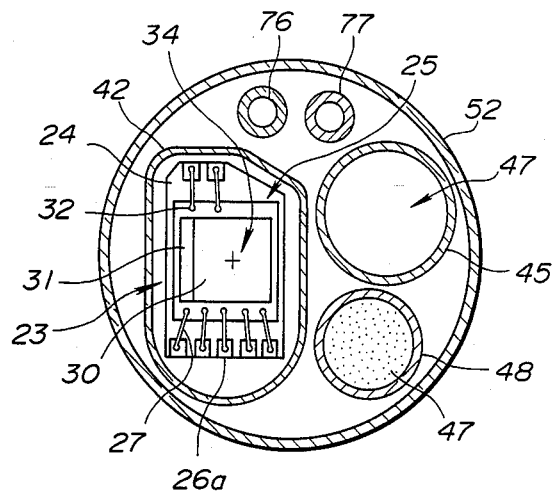
FIGS. 9 and 10 relate to the fifth embodiment of the present invention.
Figure 10:
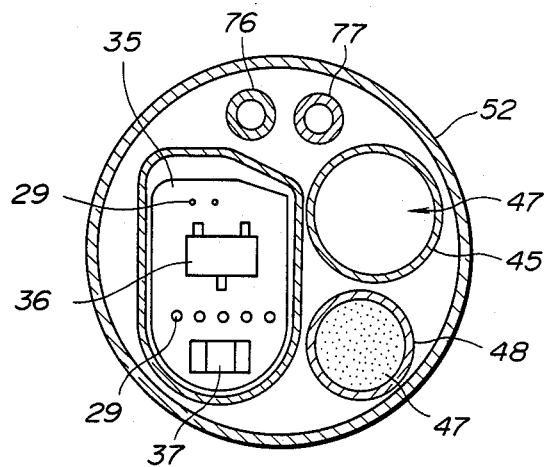

FIGS. 9 and 10 relate to the fifth embodiment of the present invention. FIG. 9 is a sectioned view of the solid state imaging device part of a tip of the insertable part of an electronic endoscope. FIG. 10 is a sectioned view of a substrate part of the tip.

In this embodiment, such bonding parts as the bonding pad 32 are formed on the two sides opposed to each other of the image area 30 of the solid state imaging device 23, the optical black row 32 is arranged on the side on which no bonding part is formed and the forceps channel 47 as the second largest component is arranged on the side reverse to this optical black row 32.

Also, in this embodiment, the shield pipe 42 is not cylindrical but is formed along the outer periphery of the solid state imaging device 23 and substrate 35. When the shield pipe 42 is cylindrical, a useless space will be produced between the image area 30 and shield pipe 42 and the image area 30 and forceps channel 47 will be separated from each other by this space part in some case. According to this embodiment, there is no useless space between the image area 30 and shield pipe 42 and the image area 30 and forceps channel 47 can be made closer to each other to make the tip 9 small in the diameter.

By the way, in the drawings, the reference numeral 76 represents a water feeding tube and 77 represents an air feeding tube.

According to the above mentioned embodiment, the second largest component smaller in the cross-sction than the solid state imaging device but larger than the other components and the image area of the above mentioned solid state imaging device can be arranged to be close to each other and, as a result, the image forming optical system and the above mentioned second largest component can be made close to each other to make the tip of the insertable part small or easy to insert into a body cavity.

It is apparent that, in this invention, working modes different in a wide range can be formed on the basis of this invention without departing from the spirit and scope of the invention. This invention is not restricted by its specific working mode except being limited by the appended claims.

What is claimed is:

1. An electronic endoscope comprising:
    a flexible insertable part formed to be small in the diameter;
    a plurality of components provided in parallel within a tip of said insertable part;
    a solid state imaging device which is one of said components and in which a solid state imaging chip having an image area provided at right angles with the lengthwise direction of the insertable part is secured on a base;
    a second largest component which has a contour smaller than the contour of said solid state imaging device but larger than the other components and in which at least a part of the contour overlaps on an imaginary circle having the smallest diameter including the contour of said solid state imaging device with the center of said image area as a center; and
    an objective system provided to have the optical axis coincide with the center of said image area.

2. An electronic endoscope according to claim 1 wherein said solid state imaging device has said solid state imaging chip secured on a disc-like base.

3. An electronic endoscope according to claim 2 wherein said base has said solid state imaging chip secured so as to be eccentric with the center of said image area.

4. An electronic endoscope according to claim 2 wherein said base is incised to conform to the contour of said second largest component.

5. An electronic endoscope according to claim 1 wherein said plurality of components include a forceps channel, a light guide and an air and water feeding channel.

6. An electronic endoscope according to claim 1 wherein said second largest component is a forceps channel.

7. An electronic endoscope according to claim 1 wherein said solid state imaging device is provided with no bonding pad near said second largest component.

8. An electronic endoscope according to claim 1 wherein said image area is rectangular.

9. An electronic endoscope according to claim 8 wherein said image area is provided with an optical black row on the farthest side of said second largest component.

10. An electronic endoscope according to claim 1 wherein a substrate fitted with electric parts is provided in parallel with said solid state imaging device in the rear of said solid state imaging device.

11. An electronic endoscope according to claim 1 wherein said substrate fitted with electric parts is included within the projected surface from the front surface of said solid state imaging device.

12. An electronic endoscope according to claim 1 wherein said solid state imaging device is covered with a cylindrical shield pipe.

13. An electronic endoscope according to claim 1 wherein said solid state imaging device is arranged so that a part of the contour may project out of the outside diameter of the insertable part.

14. An electronic endoscope according to claim 13 wherein said solid state imaging device is covered with a tip outer tube protruding in a part of the outer periphery.

15. An electronic endoscope according to claim 1 wherein a cylindrical tip body is provided at the tip of the insertable part.

16. An electronic endoscope according to claim 15 wherein said tip body is formed to be tapered in a part of the front end of the outer periphery to be made small in the diameter on the tip side.

17. An electronic endoscope according to claim 15 wherein said tip body is formed to be smaller in the outside diameter of the tip part than in the outside diameter of the rear part.

* * * * *